United States Patent [19] [11] 4,154,653
Hatakeyama et al. [45] May 15, 1979

[54] PROCESS FOR THE DEGRADATION OF HYDROXYSTYRENE POLYMERS

[75] Inventors: Hyoe Hatakeyama, Yokosuka; Takafusa Haraguchi, Tokyo; Eiichi Hayashi, Kokubunji, all of Japan

[73] Assignee: Agency of Industrial Science and Technology, Tokyo, Japan

[21] Appl. No.: 834,705

[22] Filed: Sep. 19, 1977

[30] Foreign Application Priority Data

Sep. 17, 1976 [JP] Japan .................. 52-111588

[51] Int. Cl.$^2$ .......................................... C12D 13/02
[52] U.S. Cl. .................. 195/28 R; 195/2; 195/49
[58] Field of Search .......... 195/2, 28 R, 49, 81, 195/96

[56] References Cited

U.S. PATENT DOCUMENTS 3,779,866  12/1973  Azarowicz ............................. 195/2

Primary Examiner—Alvin E. Tanenholtz

[57] ABSTRACT

Process for the degradation of hydroxystyrene polymers which comprises culturing bacteria of Moraxella genus or fungi of Penicillium genus on a medium containing a hydroxystyrene polymer having a recurring structural unit of the general formula:

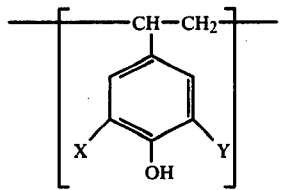

wherein X and Y each represent a hydrogen atom or an alkoxy group, as carbon source.

4 Claims, No Drawings

PROCESS FOR THE DEGRADATION OF HYDROXYSTYRENE POLYMERS

BACKGROUND OF THE INVENTION

The present invention relates to a process for the degradation of hydroxystyrene polymers.

Generally, synthetic high molecular substances are hardly decomposed by the action of microorganisms and are not susceptible of decay even when buried in soil. This nature would be a great merit of structures for which decay is undesirable. On the other hand, industrial materials not decomposable by the action of microorganisms are out of the natural recurring cycle and thus are treated compulsorily by the combustion method when thrown away as waste materials. When synthetic high molecular substances are treated by the combustion method, they are not effectively utilized and converted into substantially valueless substances, e.g. $CO_2$ and $H_2O$. Further, the treatment of such high molecular substances by combustion is attended by such a disadvantage that the combustion furnace used is susceptible of serious damage so that a specially devised furnace is required.

An essential condition for building synthetic high molecular substances, as in the case of wood, in the natural recurring cycle is that they are attacked and decomposed by microorganisms. Of the synthetic high molecular substances, polyvinyl alcohol is known to be decomposed by microorganisms. However, polyvinyl alcohol is only useful for limited purposes because of its water-soluble property and thus finds no use as ordinary plastic materials.

As a result of extensive researches on the decomposing action of various microorganisms on synthetic high molecular substances utilizable as ordinary plastic materials, it has now been found that hydroxystyrene polymers having a recurring unit similar to hydroxyphenylpropane contained as a structual unit of lignin in wood are attacked and decomposed by bacteria of Moraxella genus or fungi of Penicillium genus isolated from soil to afford industrially utilizable oxygen-containing low molecular compounds. The present invention has been accomplished on the basis of the above finding.

BRIEF SUMMARY OF THE INVENTION

Accordingly, it is a prime object of the present invention to provide a process for the degradation of frequently utilizable synthetic high molecular substances by the biochemical action of microorganisms.

It is another object of the present invention to provide a method for producing useful oxygen-containing low molecular compounds by decomposing frequently utilizable synthetic high molecular substances by the biochemical action of microorganisms.

It is still another object of the present invention to provide a method for degrading synthetic high molecular industrial wastes by the biochemical action of microorganisms.

Other and further objects, features and advantages of the present invention will become apparent more fully according to the following description.

DETAILED DESCRIPTION OF THE INVENTION

In accordance with the present invention, there is provided a process for the degradation of hydroxystyrene polymers which comprises culturing soil bacteria belonging to Moraxella genus or soil fungi belonging to Penicillium genus on a medium containing hydroxystyrene polymers having a recurring structural unit of the general formula:

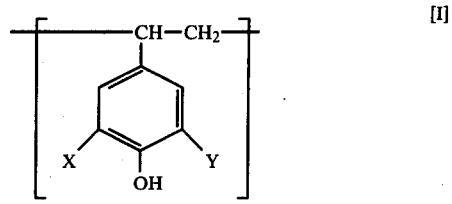

wherein X and Y each stand for a hydrogen atom or an alkoxy group, as carbon source.

The polymers having a recurring structural unit of the above general formula used in the present invention are known in literatures and prepared by oxidizing lignin obtained from the white liquor of paper mills with oxygen under alkaline conditions to form benzaldehyde derivatives, converting the benzaldehyde derivatives into the corresponding monomeric styrene derivative and polymerizing the monomers.

Below is a detailed explanation on the method for synthetizing the hydroxystyrene polymers used in the present invention.

(1) Preparation of p-hydroxystyrene polymers p-Hydroxybenzaldehyde is reacted with malonic acid to form p-hydroxycinnamic acid which is then reacted with acetic anhydride whereby the hydroxy group is acetylated. The resultant p-acetoxycinnamic acid is decarbonized to form p-acetoxystyrene which is then polymerized and hydrolyzed to produce poly(hydroxystyrene).

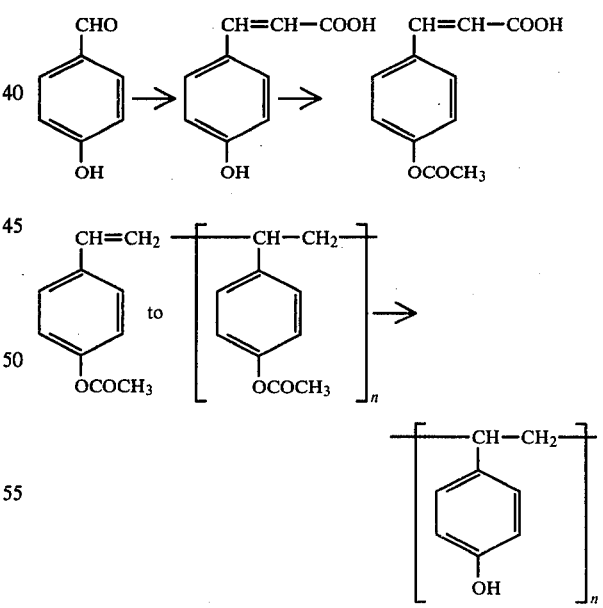

wherein n stands for a positive number corresponding to the number of monomeric units in the polymer.

(2) Preparation of 3-methoxy-4-hydroxystyrene polymer

Vaniline is reacted according to Perkin's reaction with acetic anhydride to form ferulic acid which is then decarbonized by heating to prepare 3-methoxy-4-hydroxystyrene. This compound is then acetylated with acetic anhydride, polymerized and then hydrolyzed to obtain 3-methoxy-4-hydroxystyrene polymer.

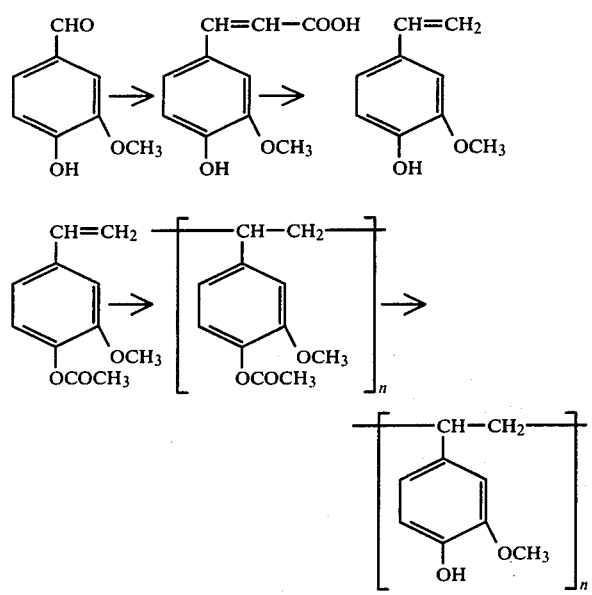

wherein n stands for a positive number corresponding to the number of monomeric units in the polymer.

(3) Preparation of 3,5-dimethoxy-4-hydroxystyrene polymer 3,5-Dimethoxy-4-hydroxystyrene polymer is obtained by repeating the process described in (2) except that 3,5-dimethoxy-4-hydroxybenzaldehyde is used as starting material in place of 3-methoxy-4-hydroxybenzadehyde.

The hydroxystyrene polymers thus obtained have a molecular weight within the range of 2,000–500,000. These polymers are used as homopolymers, copolymers or blends to manufacture various molded articles, as in the case of commonly used polystyrene. In case the polymers are used in the form of a blend, the molecular weights of the polymers are preferably within the range of 2,000–8,000 to facilitate decomposition. The molding treatment per se is conducted by any of the conventional methods such as extrusion molding, injection molding, calendering and the like.

The B-1 strain used in the present invention belongs to the Moraxella genus and is deposited with Fermentation Research Institute (one of the governmental research institutes) of 5-8-1, Inage-higashi, Chiba-ken, Japan as deposition number "FERM-R 3709". This B-1 strain is capable of growing on a culture medium with the above hydroxystrene polymer as carbon source and degrading the polymer. The bacteriological properties of the B-1 strain are as follows:

(a) Morphology:
  (1) Gram staining: negative
  (2) Shape: micrococcus-like-bacillus, 0.6μ in size, flagellous
(b) Growth on various media:
  (1) Growth on an ordinary agar medium: good
  (2) Citrate (as carbon source): +
  (3) Utility of carbohydrates:
    Glucose: − (+)
    Lactose: −
    Maltose: −
    Arabinose: +
  (4) Reduction of nitrates: −
  (5) Urease: + (urea)
(c) Physiological properties:
  (1) Movement: −
  (2) Growth in air: +
  (3) Catalase: 30 (weak)
  (4) Oxidase: + (slow)
  (5) Glucose: − (+ from 10 days after culturing)
  (6) Haemolytic property: −
  (7) Temperature range for growth: 20°–37° C.

In view of the above mentioned properties, the B-1 strain is identified as a bacterium belonging to the Moraxella genus.

The A-1 strain used in the present invention belongs to the Penicillium genus and is deposited with the aforementioned Fermantation Research Institute as deposition number "FERM-P 3882". This A-1 strain is capable of growing on a culture medium with the hydroxystyrene polymer as carbon source and degrading the polymer. The mycological properties of the A-1 strain are as follows:

(a) Morphology:

This microorganism has stalks arranged in a broomy form to which many conidiospores adhere in serial. A colony is dense and is colored in gray green and has air mycelia.

(b) Physiological properties:

Growth on various media and production of pigment are as follows (cultured at 28° C.) :
  (1) Czapek's medium
    Growth: best
    Pigment: production of a diffusible yellow pigment
  (2) Glucose-asparagine medium
    Growth: good
    Pigment: slight production of a yellow pigment
  (3) Potato-glucose agar medium
    Growth: good
    Pigment: Very poor production of a yellowish green pigment
  (4) Yeast-malt extract agar medium
    Growth: good
    Pigment: production of a yellow pigment In view of the above mentioned properties, the A-1 strain is identified as a fungus belonging to the Penicillium genus.

The products obtained by the process of the present invention wherein the biochemical action of the specific microorganism is utilized are aliphatic saturated or unsaturated polybasic carboxylic acid derivatives. The process of decomposition of the hydroxystyrene polymer is considered to proceed according the following reaction formulas:

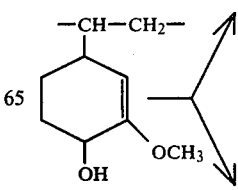

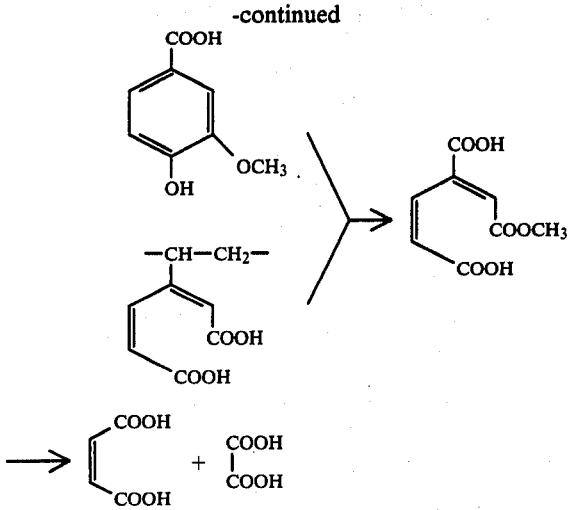

The media used to degrade the hydroxystyrene polymers according to this invention may be any of the known conventional ones so far as they necessarily contain the hydroxystyrene polymers as the main carbon source, other nutrients required for growth of the microorganisms such as nitrogen source and inorganic salts and compounds capable of promoting growth of the microorganisms. Utilizable as the nitrogen source required for growth of the microorganisms are, for example, inorganic ammonium salts such as ammonium nitrate, ammonium phosphate and ammonium sulfate as well as other nitrogen-containing compounds such as urea and ammonia per se. Examples of the nutrients include inorganic salts such as potassium dihydrogen phosphate, dipotassium hydrogen phosphate, magnesium sulfate. In addition, other metal compounds such as ferrous sulfate are added in a very small amount.

The culturing treatment is effected by merely placing the culture tank stationarily, shaking the tank or agitating the tank by aeration.

The hydrogen ion concentration during the culturing treatment is preferably between 7 and 7.5, inclusive. After completion of the culturing treatment, the microbial cells are removed by centrifugal separation and filtration and the filtrate obtained was analyzed by way of UV-absorption spectral analysis, measurement of COD value, various kinds of chromatography, mass spectroscopy and measurement of the molecular weight, whereby it was confirmed that the hydroxystyrene polymers are degraded by change in the absorption spectra, reduction of COD value, reduction of the molecular weight and identification of the low molecular weight compounds produced.

The present invention will now be explained in greater detail by way of examples.

EXAMPLE 1

Biochemical degradation of the polymers

| Composition of the medium | | |
| --- | --- | --- |
| The polymer | 1.0 | g |
| $NH_4NO_3$ | 20.0 | g |
| $CaCl_2$ | 1.0 | g |
| $KH_2PO_4$ | 1.0 | g |
| $MgSO_4 \cdot 7H_2O$ | 0.3 | g |
| $ZnSO_4$ | 0.01 | g |
| $FeSO_4$ | 0.01 | g |
| Water | 1 | liter |

| Composition of the medium | |
| --- | --- |
| pH | 7 |

(This medium will be referred to hereinafter as PHS medium.)

One hundred milliliters of the medium were placed in a flask and sterilized at 115°–119° C. for 15 minutes. A very small amount (one platinum loop) of Moraxella B-1 strain which had been growing on another PHS medium was innoculated on this PHS medium and cultured at 28° C. The change in the mean molecular weight with the lapse of time of the polymer contained in the culture solution was analyzed by way of gel permeation chromatography.

When p-hydroxystyrene polymer was used as carbon source in the medium, the portion of the polymer corresponding to a molecular weight of 240 (almost a dimer) was found removed from the original polymers with a mean molecular weight of about 1800 (pentadecamer) after culturing for 20 days.

When 3-methoxy-4-hydroxystyrene polymer was used as carbon source in the medium, the original polymer with a mean molecular weight of about 2100 (tridecamer) was degraded to a polymer with a mean molecular weight of about 1600 after culturing for 4 days but showed a tendency of increasing the molecular weight after culturing for 20 days. In this case, however, the proportion of oligomers not greater than hexamer was increased and the formation of oxalic acid and maleic acid was detected. Such increase in molecular weight during the culturing treatment is interpreted as a result of opening of the benzene rings in the polymer and subsequent oxidation to carboxylic acid.

The above mentioned polymers showed UV-absorption spectral bands indicating the existence of aromatic rings but the spectral bands were weakened with the lapse of time, thus indicating that the aromatic rings were opened gradually.

The B-1 strain was cultured in a similar manner to that described above, on a film of a p-hydroxystyrene polymer (Mw = $2 \times 10^5$) for 20 days. The cultured film was then subjected to an IR-absorption spectral analysis whereby a clear absorption band of C=O was found, thus indicating degradation of the polymer.

EXAMPLE 2

In the same manner as described in Example 1, 100 ml of the PHS medium was placed in a flask and sterilized, and thereafter a very small amount of Penicillium A-1 strain was innoculated on the PHS medium and cultured.

When 3,5-dimethoxy-4-hydroxystyrene polymer was used as carbon source in the medium, a portion corresponding to one monomer was found removed from the original polymer with a mean molecular weight of about 1100 (pentamer) after culturing for 20 days. The above polymer showed, on UV-absorption spectral analysis, characteristic absorption bands of aromatic rings. These absorption bands were, however, weakened with the lapse of time, thus showing that the aromatic rings were gradually opened.

An IR-absorption spectral analysis of the culture product showed a peak absorption band at 1700 cm$^{-1}$ due to the existence of carbonyl groups which was intensified with the lapse of time, indicating that the original polymer was degraded to a product having carbonyl groups. An IR-aborption spectral analysis of the product after culturing for an extended period of time revealed the presence of oxalic acid, indicating that the aforementioned polymer was finally degraded to oxalic acid.

It is understood that the preceding representative examples may be varied within the scope of the present specification, both as to ingredients and culturing conditions, by one skilled in the art to achieve essentially the same results.

As many widely different embodiments of this invention may be made without departing from the spirit and scope thereof, it is to be understood that this invention is not limited to the specific embodiments thereof except as defined in the appended claims.

What is claimed is:

1. A process for the degradation of hydroxystyrene polymers which comprises culturing for a time sufficient to effect said degradation a microorganism selected from the group consisting of Moraxella strain FERM-R3709 and Penicillium strain FERM-P3882 on a medium containing a hydroxystyrene polymer having a recurring structural unit of the general formula:

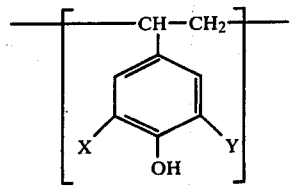

wherein X and Y each represent a hydrogen atom or an alkoxy group, as carbon source.

2. A process according to claim 1 wherein said hydroxystyrene polymer is p-hydroxystyrene polymer.

3. A process according to claim 1 wherein said hydroxystyrene polymer is 3-methoxy-4-hydroxystyrene polymer.

4. A process according to claim 1 wherein said hydroxystyrene polymer is 3,5-dimethoxy-4-hydroxystyrene polymer.